United States Patent
Lalla et al.

(10) Patent No.: US 12,251,378 B2
(45) Date of Patent: Mar. 18, 2025

(54) LONG-ACTING LOCAL ANESTHETIC FORMULATION

(71) Applicant: UNIVERSITY OF CONNECTICUT, Farmington, CT (US)

(72) Inventors: Rajesh V. Lalla, West Hartford, CT (US); Diane J. Burgess, Storrs, CT (US); Tingting Li, Mansfield Center, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 875 days.

(21) Appl. No.: 17/053,553

(22) PCT Filed: May 8, 2019

(86) PCT No.: PCT/US2019/031291
§ 371 (c)(1),
(2) Date: Nov. 6, 2020

(87) PCT Pub. No.: WO2019/217536
PCT Pub. Date: Nov. 14, 2019

(65) Prior Publication Data
US 2021/0228556 A1    Jul. 29, 2021

Related U.S. Application Data

(60) Provisional application No. 62/668,370, filed on May 8, 2018.

(51) Int. Cl.
A61K 31/445    (2006.01)
A61K 9/00      (2006.01)
(Continued)

(52) U.S. Cl.
CPC .......... *A61K 31/445* (2013.01); *A61K 9/0014* (2013.01); *A61K 9/006* (2013.01);
(Continued)

(58) Field of Classification Search
None
See application file for complete search history.

(56) References Cited

U.S. PATENT DOCUMENTS

| | | |
|---|---|---|
| 6,004,578 A | 12/1999 | Lee et al. |
| 6,515,016 B2 | 2/2003 | Hunter |

(Continued)

FOREIGN PATENT DOCUMENTS

| | | | |
|---|---|---|---|
| EP | 3173067 A | 11/2015 | |
| JP | 2016185950 A | * 10/2016 | .......... A61K 31/167 |
| WO | 2012135422 A2 | 10/2012 | |

OTHER PUBLICATIONS

Ferreira et al. Linear correlation between rheological, mechanical and mucoadhesive properties of polycarbophil polymer blends for biomedical applications. Journal of the mechanical behavior of biomedical materials 68 (2017) 265-275 (Year: 2017).*

(Continued)

*Primary Examiner* — Lakshmi S Channavajjala
(74) *Attorney, Agent, or Firm* — Lisa Mueller; Casimir Jones SC

(57) ABSTRACT

Compositions that include a bupivacaine salt are provided. The compositions may include bupivacaine linoleate, bupivacaine linolenate or bupivacaine laurate, at least one thermosensitive polymer, and at least one mucoadhesive or dermoadhesive agent. Also provided are methods for the treatment of an inflammatory or ulcerative condition with the disclosed compositions.

12 Claims, 4 Drawing Sheets

(51) Int. Cl.
*A61K 9/70* (2006.01)
*A61K 47/32* (2006.01)
*A61K 47/34* (2017.01)
*A61K 47/38* (2006.01)
*A61P 23/02* (2006.01)

(52) U.S. Cl.
CPC ............ *A61K 9/7015* (2013.01); *A61K 47/32* (2013.01); *A61K 47/34* (2013.01); *A61K 47/38* (2013.01); *A61P 23/02* (2018.01)

(56) References Cited

U.S. PATENT DOCUMENTS

| | | |
|---|---|---|
| 8,822,410 B2 | 9/2014 | Simons et al. |
| 9,464,051 B2 | 10/2016 | Kandula |
| 10,227,301 B2 | 3/2019 | Kandula |
| 2004/0009212 A1 | 1/2004 | Tsai |
| 2006/0293216 A1* | 12/2006 | Klaveness ............... A61P 29/00 424/468 |
| 2017/0296485 A1* | 10/2017 | Kottayil ................. A61K 47/22 |

OTHER PUBLICATIONS

International Application No. PCT/US2019/031291, "International Preliminary Report on Patentability", May 22, 2020, 7 pages.
International Application No. PCT/US2019/031291, "International Search Report and Written Opinion", Jul. 15, 2019, 8 pages.
Cavallari Cristina et al: "Mucoadhesive multiparticulate patch for the intrabuccal controlled delivery of lidocaine", European Journal of Pharmaceutics and Biopharmaceutics, Elsevier Science Publishers B.V., Amsterdam, NL, vol. 83, No. 3, Nov. 16, 2012 (Nov. 16, 2012), pp. 405-414, XP029001862.
European Patent Office, Extended European search report for European Application No. 19799214.2 mailed Jan. 27, 2022.

* cited by examiner

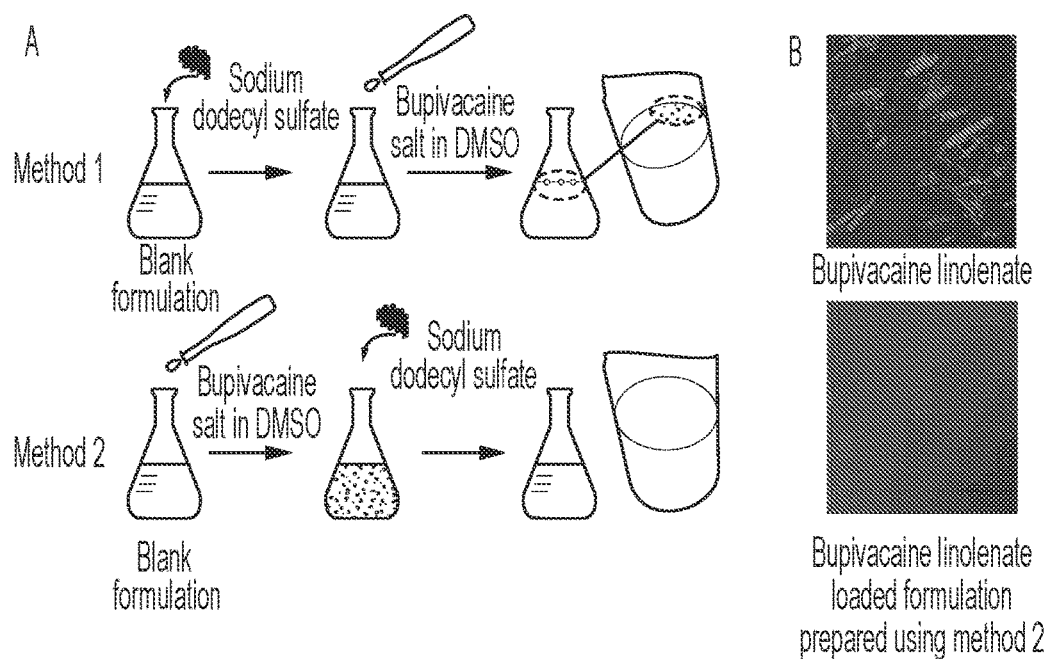
FIGURE 6
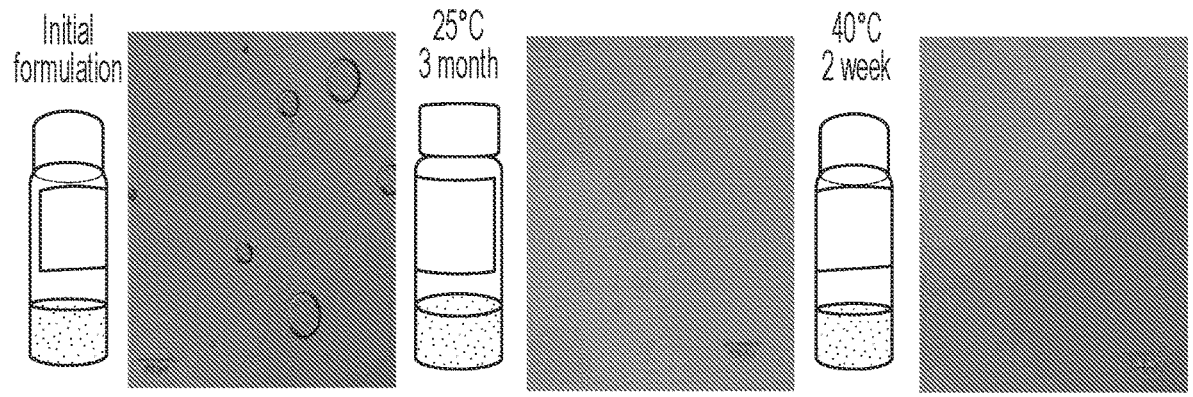

LONG-ACTING LOCAL ANESTHETIC FORMULATION

CROSS-REFERENCE TO RELATED APPLICATIONS

This application is a U.S. national phase of International Patent Application No. PCT/US2019/031291 filed on May 8, 2019, which claims priority to U.S. Patent Application No. 62/668,370, filed on Mar. 8, 2018. The entire contents of both applications are hereby incorporated herein by this reference.

FIELD

Embodiments of the present disclosure relate generally to compositions including a bupivacaine salt. In particular, compositions and methods for treating inflammatory or ulcerative mucosal and skin conditions are provided.

BACKGROUND

Significant local pain is associated with inflammatory and ulcerative mucosal and skin conditions. For example, oral mucositis (OM) is a painful condition involving erythema and ulceration of the oral mucosa, which occurs as a side-effect of cancer treatment. OM can occur secondary to systemic chemotherapy for various cancers and/or secondary to radiation therapy (RT) for head and neck (H&N) cancer. OM affects approximately 20-40% of patients receiving conventional chemotherapy regimens for solid tumors, about 80% of patients receiving high-dose chemotherapy in preparation for a hematopoietic stem cell transplant (HSCT), and almost 100% of patients receiving therapeutic RT for H&N cancer. The pathogenesis of OM is complex and includes not only direct damage to oral epithelial cells by cancer therapy, but also upregulation of inflammatory pathways, and secondary infection of the oral ulcerations, both of which can further aggravate the severity of OM.

Due to the intense pain caused by OM lesions, patients may be unable to continue eating by mouth and may require feeding intravenously or through a stomach tube. Many patients receiving RT for H&N cancer have a stomach tube surgically placed prophylactically before the start of RT. The nutritional compromise leads to weight loss, impaired healing, reduced resistance to infection, and a general failure to thrive. Secondary infection of the lesions can result in not only local infection, but also potentially life-threatening systemic sepsis in patients immunosuppressed due to chemotherapy. In addition, severe OM can necessitate undesirable dose-reductions or treatment breaks in cancer therapy which can negatively affect cancer prognosis.

Pain is the primary complaint of patients suffering with OM; however, the options available for pain control are sub-optimal. The current first-line therapy at most U.S. hospitals is a mouth rinse containing the local anesthetic lidocaine, usually combined with other ingredients such as diphenhydramine and a coating agent such as Maalox. However, this rinse provides only short-term relief (e.g., less than 30 minutes), and many patients need systemic opioids instead to manage the pain. Opioids have significant side-effects including somnolence, constipation, and risk of addiction. Other products available are topical coating agents (which may form a protective barrier over oral ulcerations, but do not contain an anesthetic) and gel-based products for relief from mild oral soft tissue pain for a short period of time (which are too weak to be effective for oral mucositis). In addition, lozenges containing bupivacaine hydrochloride are being tested; however, lozenges do not provide a long duration of relief, and many patients with OM would not be able to tolerate a lozenge due to dry mouth, and the potential for additional trauma to the ulcerations and oral mucosa. Therefore, the field lacks a practical solution for the targeted delivery of medication for a longer duration of pain relief in patient's suffering from oral mucositis or other inflammatory or ulcerative mucosal and skin conditions.

SUMMARY

Methods and compositions are provided for the long-acting local administration of an anesthetic for treatment of mucositis or other inflammatory or ulcerative mucosal or skin conditions. Provided herein are pharmaceutical formulations including a bupivacaine salt. The pharmaceutical formulations may include bupivacaine linoleate, bupivacaine linolenate or bupivacaine laurate, at least one thermosensitive polymer, and at least one mucoadhesive or dermoadhesive agent. In some embodiments, the bupivacaine linoleate is present at a concentration of about 0.5 mg/mL to about 10 mg/mL or about 0.1% weight/volume (w/v) to about 2% w/v. In one embodiment, the bupivacaine linoleate is present at a concentration of about 2 mg/mL or 0.4% w/v. In certain embodiments, the at least one thermosensitive polymer is poloxamer or poloxamine. In some embodiments, the thermosensitive polymer is present at a concentration of about 10% w/v to about 22% w/v. In some embodiments, the pharmaceutical formulation includes two or more thermosensitive polymers. In certain embodiments, the pharmaceutical formulation includes poloxamer 407 and poloxamer 188. In some embodiments, the pharmaceutical formulation is a liquid at about 25° C. and forms a semi-solid gel at about 37° C. In certain embodiments, the pharmaceutical formulation comprises a gelation temperature of about 30° C. to about 37° C. In some embodiments, the mucoadhesive or dermoadhesive agent is selected from the group consisting of polyethylene glycol, caprylic glyceride, capric glyceride, vinyl polymer, methyl cellulose, ethyl cellulose, hydroxyethyl cellulose, hydroxypropyl cellulose, hydroxypropylmethyl cellulose, carboxymethyl cellulose, alginic acid, sodium alginate, acrylic acid polymer, and carbopol polymer. In some embodiments, the mucoadhesive or dermoadhesive agent comprises carboxymethylcellulose. In a particular embodiment, the mucoadhesive or dermoadhesive agent is present at a concentration of about 0.05% w/v to about 5% w/v. In some embodiments, the mucoadhesive or dermoadhesive agent includes at least one acrylic acid polymer or carbopol polymer. In certain embodiments, the acrylic acid polymer or carbopol polymer may be present at a concentration of about 0.04% w/v to about 1% w/v. In some embodiments, the pharmaceutical formulation includes bupivacaine linoleate, poloxamer 407, poloxamer 118, and Carbopol® 971P (an acrylic acid polymer). In some embodiments, the pharmaceutical formulation includes bupivacaine linoleate, poloxamer 407, poloxamer 118, and Carbopol® 974P (an acrylic acid polymer). In some embodiments, the composition includes bupivacaine linoleate, bupivacaine linolenate or bupivacaine laurate, poloxamer 407, poloxamer 118, and Noveon® AA-I polycarbophil (an acrylic acid polymer). In some embodiments, the pharmaceutical formulations include at least one pharmaceutically acceptable excipient, such as a flavoring agent, sweetener, sweet enhancer, preservative, stabilizer, or solubilizer. In one embodiment, the pharmaceutical formulation may be a spray formulation. In another embodiment, the pharmaceutical formulation may be a topical formulation. In some embodiments, the pharmaceutical formulation releases bupivacaine linoleate for up to about 2 hours to about 4 hours.

Also provided is a spray formulation comprising bupivacaine linoleate, bupivacaine linolenate or bupivacaine laurate at a concentration of about 0.1% weight/volume (w/v) to about 2% w/v, at least one thermosensitive polymer at concentration of about 10% w/v to about 22% w/v, and a mucoadhesive or dermoadhesive agent at a concentration of about 0.05% w/v to about 5% w/v. In some embodiments, the at least one thermosensitive polymer is poloxamer or poloxamine. In some embodiments, the mucoadhesive or dermoadhesive agent is selected from the group consisting of polyethylene glycol, caprylic glyceride, capric glyceride, vinyl polymer, methyl cellulose, ethyl cellulose, hydroxyethyl cellulose, hydroxypropyl cellulose, hydroxypropylmethyl cellulose, carboxymethyl cellulose, alginic acid, sodium alginate, acrylic acid polymer, and carbopol polymer. In some embodiments, the pharmaceutical formulations include at least one pharmaceutically acceptable excipient, such as a flavoring agent, sweetener, sweet enhancer, preservative, stabilizer, or solubilizer. In some embodiments, the pharmaceutical formulation releases bupivacaine linoleate, bupivacaine linolenate or bupivacaine laurate for up to about 2 hours to about 6 hours.

Methods for treating a subject having an inflammatory disease or condition are provided, including administering to the subject an effective amount of a pharmaceutical formulation comprising a bupivacaine salt. In some embodiments, the methods include administering to the subject an effective amount of a pharmaceutical formulation comprising bupivacaine linoleate, at least one thermosensitive polymer, and at least one mucoadhesive or dermoadhesive agent. In certain aspects, the disease or condition is oral mucositis. In some embodiments, the pharmaceutical formulation may be administered to the mucosa or skin. In certain embodiments, the pharmaceutical formulation may be administered by transmucosal delivery, sublingual delivery, via the buccal cavity, via mucosal membranes, or via the gastrointestinal tract. In some embodiments, the pharmaceutical formulation is administered as a spray formulation. In certain aspects, the pharmaceutical formulation may be administered as more than one spray of the spray formulation. In some embodiments, the pharmaceutical formulation releases bupivacaine linoleate, bupivacaine linolenate or bupivacaine laurate for up to about 2 hours to about 6 hours. In some embodiments, the bupivacaine linoleate is present at a concentration of about 0.5 mg/mL to about 10 mg/mL or about 0.1% weight/volume (w/v) to about 2% w/v. In one embodiment, the bupivacaine linoleate is present at a concentration of about 2 mg/mL or 0.4% w/v. In certain embodiments, the at least one thermosensitive polymer is poloxamer or poloxamine. In some embodiments, the thermosensitive polymer is present at a concentration of about 10% w/v to about 22% w/v. In some embodiments, the pharmaceutical formulation includes two or more thermosensitive polymers. In certain embodiments, the pharmaceutical formulation includes poloxamer 407 and poloxamer 188. In some embodiments, the composition is a liquid at about 25° C. and forms a semi-solid gel at about 37° C. In certain embodiments, the pharmaceutical formulation comprises a gelation temperature of about 30° C. to about 37° C. In some embodiments, the mucoadhesive or dermoadhesive agent is selected from the group consisting of polyethylene glycol, caprylic glyceride, capric glyceride, vinyl polymer, methyl cellulose, ethyl cellulose, hydroxyethyl cellulose, hydroxypropyl cellulose, hydroxypropylmethyl cellulose, carboxymethyl cellulose, alginic acid, sodium alginate, acrylic acid polymer, and carbopol polymer. In some embodiments, the mucoadhesive or dermoadhesive agent comprises carboxymethylcellulose. In a particular embodiment, the mucoadhesive or dermoadhesive agent is present at a concentration of about 0.05% w/v to about 5% w/v. In some embodiments, the mucoadhesive or dermoadhesive agent includes at least one acrylic acid polymer or carbopol polymer. In certain embodiments, the acrylic acid polymer or carbopol polymer may be present at a concentration of about 0.04% w/v to about 1% w/v. In some embodiments, the pharmaceutical formulation includes bupivacaine linoleate, poloxamer 407, poloxamer 118, and Carbopol® 971P (an acrylic acid polymer). In some embodiments, the pharmaceutical formulation includes bupivacaine linoleate, poloxamer 407, poloxamer 118, and Carbopol® 974P (an acrylic acid polymer). In some embodiments, the pharmaceutical formulation includes bupivacaine linoleate, poloxamer 407, poloxamer 118, and Noveon® AA-1 polycarbophil (an acrylic acid polymer). In some embodiments, the pharmaceutical formulation includes bupivacaine linolenate, poloxamer 407, poloxamer 118, and Carbopol® 974P (an acrylic acid polymer). In some embodiments, the pharmaceutical formulations include at least one pharmaceutically acceptable excipient, such as a flavoring agent, sweetener, sweet enhancer, preservative, stabilizer, or solubilizer. In some embodiments, the pharmaceutical formulation includes bupivacaine linolenate, poloxamer 407, poloxamer 118, Carbopol® 974P (an acrylic acid polymer) and mint flavor. In some embodiments, the pharmaceutical formulation includes bupivacaine linolenate, poloxamer 407, poloxamer 118, Carbopol® 974P (an acrylic acid polymer) and raspberry flavor.

DESCRIPTION OF THE DRAWINGS

The present application includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

FIG. 5A is a flow chart with photographs showing loading of bupivacaine salt to blank formulations prepared by two different methods. FIG. 5B is a photomicrograph of the polarized light microscopy results of pure bupivacaine linolenate and a formulation loaded with bupivacaine linolenate using Method 2 of FIG. 5A.

FIG. 6 is a series of photographs showing the appearance and polarized light microscopy results of formulation SCP-2 at different storage conditions.

DETAILED DESCRIPTION

Figure 1:
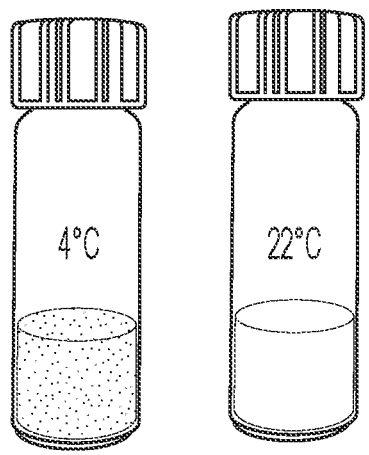
FIG. 1 is a photograph of an exemplary embodiment of a disclosed bupivacaine linoleate formulation produced at different temperatures. The vial on the left was prepared at 4±1° C. and resulted in drug precipitation. The vial on the right was prepared at about 22±1° C.

The following description recites various aspects and embodiments of the disclosed compositions and methods. No particular embodiment is intended to define the scope of the compositions and methods. Rather, the embodiments merely provide non-limiting examples that are at least included within the scope of the disclosed compositions and methods. The description is to be read from the perspective of one of ordinary skill in the art; therefore, information well known to the skilled artisan is not necessarily included. It is also to be understood that as used herein, the singular forms "a," "and," and "the" include plural references unless the context clearly dictates otherwise.

Pharmaceutical Formulations

Provided herein are compositions and methods for the treatment of inflammatory or ulcerative conditions in a subject. In particular, the compositions comprise bupivacaine linoleate, bupivacaine linolenate or bupivacaine laurate. In some embodiments, the compositions comprise bupivacaine linoleate, at least one thermosensitive polymer, and at least one mucoadhesive or dermoadhesive agent. In some embodiments, the compositions include bupivacaine linolenate, at least one thermosensitive polymer, and at least one mucoadhesive or dermoadhesive agent. As used herein, bupivacaine linoleate is a bupivacaine salt of linoleic acid and is described, for example, in U.S. Pat. No. 9,464,051. As used herein, bupivacaine linolenate is a bupivacaine salt of linolenic acid and is described, for example, in U.S. Pat. No. 9,464,051. As used herein, bupivacaine laurate is a bupivacaine salt of lauric acid and is described, for example, in U.S. Pat. No. 9,464,051. In some embodiments, the bupivacaine linoleate, bupivacaine linolenate or bupivacaine laurate is present at a concentration of about 0.5 mg/mL to about 13 mg/mL or about 0.1% weight/volume (w/v) to about 2% w/v of the formulation. In other embodiments, the bupivacaine linoleate is present at a concentration of about 0.6 mg/mL to about 8 mg/mL, about 0.7 mg/mL to about 7 mg/mL, about 0.8 mg/mL to about 6 mg/mL, about 0.9 mg/mL to about 5 mg/mL, about 1 mg/mL to about 4 mg/mL, or about 1.5 mg/mL to about 3 mg/mL. In some embodiments, the bupivacaine linoleate is present at a concentration of about 2 mg/mL to about 6 mg/mL. In one embodiment, the bupivacaine linoleate is present at a concentration of about 2 mg/mL or 0.4% w/v of the formulation.

As used throughout, a "thermosensitive polymer" refers to an ingredient that may be used to obtain a free-flow liquid formulation at about storage conditions (e.g., 25° C.) and to obtain a semi-solid gel formulation at about physiological conditions (e.g., 37° C.). In certain aspects, the gelation property is characterized by gelation temperatures of about 30° C. to about 37° C., about 31° C. to about 37° C., about 32° C. to about 37° C., or about 33° C. to about 36° C. As used herein, the term "gelation temperature" refers to the temperature at which a liquid composition begins to solidify, and the "gelation time" refers to the time it takes for a liquid composition to begin to solidify. In certain aspects, the gelation time is about a few seconds to about 2 minutes, about 30 seconds to about 2 minutes, or about 45 seconds to about 90 seconds from storage temperature to the temperature at the target mucosa or skin (e.g., from storage at room temperature of about 25° C. to oral mucosa temperature of about 37° C.). In one preferred embodiment, the formulation has a gelation temperature of about 34° C. to about 36° C., and a gelation time of about 60 seconds.

Preferably, the thermosensitive polymer material is a pharmaceutically acceptable and biodegradable ingredient. Thermosensitive polymers suitable for the disclosed compositions may include, but are not limited to, poloxamer and poloxamine. In other aspects, the thermosensitive polymer may include but is not limited to, Poly (N-isopropylacrylamide) and its derivatives, chitosan/polyol salt combinations, chitosan/glycerophosphate combinations, carboxymethylhexanoyl chitosan and its derivatives, xyloglucan and its derivatives, poly(organophosphazene) and its derivatives, 2-(dimethylamino) ethyl methacrylate and its derivatives, poly(ethylene glycol) conjugates with another polymer such as poly(ethylene glycol)-poly(lactic-co-glycolic acid), poly (ethylene glycol)-poly(e-caprolactone), poly(ethylene glycol)-poly(N-(2-hydroxypropyl) methacrylamide lactate), poly(ethylene glycol)-polylactide, poly(ethylene glycol)-poly-((R)-3-hydroxybutyrate)-poly(propylene glycol), or poly(e-caprolactone-co-lactide)-poly(ethylene glycol)-poly (e-caprolactone-co-lactide). In one embodiment, the pharmaceutical formulation contains poloxamer 407 as the thermosensitive polymer. In certain embodiments, the thermosensitive polymer is present in the pharmaceutical formulation at a concentration of about 10% w/v to 22% w/v of the formulation. In other embodiments, the thermosensitive polymer is present in the pharmaceutical formulation at a concentration of about 12% w/v to 20% w/v, about 14% w/v to 18% w/v, or about 15% w/v to 17% w/v of the formulation. In some embodiments, the disclosed pharmaceutical formulations include at least one thermosensitive polymer. The disclosed pharmaceutical formulations may contain two or more thermosensitive polymers. The ratio of the mixing polymers can be adjusted by those skilled in the art according to the physiological conditions in the target mucosa or skin. In one embodiment, the pharmaceutical formulation includes both poloxamer 407 and poloxamer 188. In certain embodiments, the pharmaceutical formulation includes poloxamer 407 and poloxamer 188 at a concentration of about 20% w/v and about 2% w/v, respectively, yielding a gelation temperature of about 36° C. In certain embodiments, the pharmaceutical formulation includes poloxamer 407 at a concentration of about 14% w/v to about 22% w/v, about 15% w/v to about 20% w/v, or about 16% w/v to about 18% w/v of the formulation, and includes poloxamer 188 at a concentration of about 1% w/v to about 6% w/v, about 2% w/v to about 6% w/v, or about 3% w/v to about 5% w/v of the formulation.

As used throughout, a "mucoadhesive or dermoadhesive agent" or "mucoadhesive or dermoadhesive polymer" refers to an ingredient that may be used to increase the adhesion of the pharmaceutical formulation to the target mucosa or skin for a protracted period of time. The disclosed pharmaceutical formulations comprise at least one mucoadhesive or dermoadhesive agent to enable the pharmaceutical formulation to achieve a lengthened duration on the applied surface of the target mucosa or skin. In some embodiments, the disclosed pharmaceutical formulations may comprise two or more mucoadhesive or dermoadhesive agents. Preferably, the mucoadhesive or dermoadhesive agents are pharmaceutically acceptable. Mucoadhesive or dermoadhesive agents suitable for the disclosed pharmaceutical formulations may include, but are not limited to, polyethylene glycol caprylic/capric glycerides, vinyl polymers, cellulosic derivatives (methyl cellulose, ethyl cellulose, hydroxyethyl cellulose, hydroxypropyl cellulose, hydroxypropylmethyl cellulose and carboxymethyl cellulose), polysaccharides (alginic acid and sodium alginate) or polyacrylic acid (carbopols). In certain embodiments, the formulations include carboxymethyl cellulose. In certain embodiments, the carboxymethyl cellulose is present at a concentration of about 0.05% w/v to 5% w/v. In other specific embodiments, the carboxymethyl cellulose is present at a concentration of at a concentration of about 0.1% w/v to about 4% w/v, about 0.5% w/v to about 3% w/v, or about 1% w/v to about 2% w/v of the formulation. In some embodiments, the pharmaceutical formulations include at least one acrylic acid polymer or carbopol. As used herein, an "acrylic acid polymer" may include Carbopol® polymers, Pemulen™ polymeric emulsifiers, and Noveon® polycarbophils or calcium polycarbophils. As used herein, a Carbopol® polymer is a polymer of acrylic acid cross-linked with polyalkenyl ethers or divinyl glycol. As used herein, a Noveon® polycarbophil is a high molecular weight acrylic acid polymer cross-linked with divinyl glycol. In certain embodiments, the at least one acrylic acid polymer or carbopol polymer may include, but is not limited to, Carbopol® 971P, Carbopol® 974P, or Noveon® AA-1 polycarbophil. In certain embodiments, the compositions include one or more acrylic acid polymers or carbopols at a total concentration of about 0.04% w/v to 1% w/v of the formulation. In other specific embodiments, the compositions may include one or more acrylic acid polymers or carbopols at a total concentration of about 0.05% w/v to about 0.5% w/v, about 0.06% w/v to about 0.25% w/v, or about 0.07% w/v to about 0.1% w/v of the formulation.

In some embodiments, the pharmaceutical formulation includes at least one pharmaceutically acceptable excipient. Excipients suitable for the disclosed compositions may include, but are not limited to, flavoring agents, sweeteners, sweet enhancers, preservatives, solubilizers, as well as some stabilizers. In some aspects, the flavoring agent may include, but is not limited to, vanillin, almond oil, DL-menthol, peppermint oil, spearmint oil, methyl salicylate, bubblegum, mint flavoring or fruit flavoring. In certain embodiments, the formulations include mint flavoring. In certain embodiments, the mint flavoring is present at a concentration of about 0.5% w/v. In certain embodiments, the formulations include raspberry flavoring. In certain embodiments, the raspberry flavoring is present at a concentration of about 0.5% w/v. In some aspects, the sweetener may include, but is not limited to, saccharin, acesulfame, aspartame, neotame, sucralose, glycerol, propylene glycol, sorbitol, sucrose, syrup, tagatose, mannitol, maltose, maltitol, galactose, fructose, erythritol, or dextrose. The preservative may include, but is not limited to, benzyl alcohol, benzalkonium chloride, phenyl mercuric acetate, or phenylethyl alcohol. In some aspects, the solubilizer may include, but is not limited to, purified diethylene glycol monoethyl ether, cyclodextrins, glycerol monostearate, lecithin, poloxomer, polyethylene alkyl ethers, polyoxyethylene castor oil derivatives, polyoxyethylene sorbitan fatty acid esters, polyoxyethylene stearates, stearic acid, citric acid, and ascorbic acid and the like; surface active agents such as polysorbates, sorbiton esters, polyvinyl alcohol, benzal konium chloride, benzithonium chloride, cetrimide, docusate sodium, sodium lauryl sulphate, or octoxynol. In some embodiments, the stabilizer may include, but is not limited to, sodium metabisulphite, sodium bisulphite, disodium EDTA, or ascorbic acid. Suitable nontoxic pharmaceutically acceptable carriers for use in formulations can be found in Remington's Pharmaceutical Sciences, 17th Edition, 1985. It will be appreciated by persons skilled in the art that the excipients and/or additives aforementioned are provided merely by way of example and that various other such components may be used in the formulation.

The disclosed formulations may have a pH of about 4.0 to about 8.0. In one aspect, the pH of the formulation may be about pH 5.5, about pH 6.0, about pH 6.5, about pH 7.0, or about pH 7.5. In another aspect, the pH of the formulation the may be about pH 4.0. The formulation as disclosed may be formulated as a spray formulation or topical formulation by virtue of its thermosensitive property. A variety of metered dose delivery devices may be adapted for the administration of a spray as described in the present invention. In one embodiment, the spray volume of the formulation per actuation is about 80 µL to about 120 µL, about 90 µL to about 110 µL., or about 95 µL to about 105 µL. In another embodiment, the spray volume of the formulation per actuation is about 170 µL to about 220 µL, about 180 µL to about 210 µL, or about 190 µL to about 200 µL. Those skilled in the art will appreciate that the dose in each spray can be adjusted by either using a different device or adjusting the bupivacaine linoleate concentration in the formulation. The number of sprays could be easily calculated by the dose required and the dose per actuation. In one aspect, more than one spray of the oral spray formulation may be administered to a patient. The formulations as disclosed may be formulated to release bupivacaine linoleate of about 80% within 2 hours, within 4 hours, and within 6 hours to maintain anesthesia for at least 4 hours, at least 6 hours, and at least 8 hours (given the drug half-life). The formulations as disclosed herein may be formulated to release bupivacaine linolenate of about 80% within 2 hours, within 4 hours, and within 6 hours to maintain anesthesia for at least 8 hours (given the drug half-life).

The formulation disclosed herein is formulated for delivery to mucosa and skin. In certain embodiments, the formulation may be delivered transmucosally, sublingually, via the buccal cavity, via mucosal membranes and/or through the gastrointestinal tract. In a preferred embodiment, the oral mucosal delivery of the formulations can be used for oral mucositis.

Methods for Use of the Pharmaceutical Formulations

Also provided are methods for treating a subject having an inflammatory disease or condition, including administering to the subject an effective amount of a pharmaceutical formulation comprising bupivacaine linoleate. As used herein, the terms "treat" or "treating" or "treatment" can refer to one or more of: delaying the progress of a disease, disorder, or condition; controlling a disease, disorder, or condition; ameliorating one or more symptoms characteristic of a disease, disorder, or condition; or delaying the recurrence of a disease, disorder, or condition, or characteristic symptoms thereof, depending on the nature of the disease, disorder, or condition and its characteristic symptoms. As used throughout, the term "subject" or "patient" refers to an individual. The term "subject" does not require one to have any particular status with respect to a hospital, clinic, or research facility (e.g., as an admitted patient, a study participant, or the like). Preferably, the subject is a mammal such as a primate, and, more preferably, a human of any age. Non-human primates may be subjects as well. The term subject also may include domesticated animals (e.g., cats, dogs), livestock (e.g., cattle, horses, pigs, sheep, goats), and laboratory animals (e.g., ferret, chinchilla, mouse, rabbit, rat, gerbil, guinea pig). Thus, veterinary uses are contemplated herein.

As used throughout, the term "inflammatory or ulcerative condition" is used to refer to diseases or conditions that include the inflammation and/or ulceration of the skin or mucosa. In one embodiment, the inflammatory or ulcerative condition is mucositis. In a particular embodiment, the condition is oral mucositis that occurs as a side-effect of cancer treatment. In another embodiment, the condition is an ulcerative condition associated with HIV infection. In some embodiments, the condition is a mucosal or skin condition. In some embodiments, the condition may include, but is not limited to, aphthous stomatitis (canker sores), traumatic ulcerations, herpes or other viral infection, candidiasis or other fungal infection, bacterial infection, erythema migrans, erosive lichen planus, diabetic ulcers, pressure ulcers, blistering skin diseases, pemphigus vulgaris, mucous membrane pemphigoid, erythema multiforme/Stevens-Johnson syndrome/toxic epidermal necrolysis, and other skin or mucosal erosive and/or ulcerative conditions.

As used herein, the term "effective amount" is an amount sufficient to induce a desired therapeutic effect in a subject to whom the compound is administered. In some embodiments, the desired therapeutic effect is a decrease in pain and/or inflammation associated with the disease or condition. In some aspects, an effective amount is an amount sufficient to induce a decrease in pain and/or inflammation in the subject for at least two hours to about four hours. In some embodiments, the pharmaceutical formulation for use in the disclosed methods comprises bupivacaine linoleate, at least one thermosensitive polymer, and at least one mucoadhesive or dermoadhesive agent. In some embodiments, the pharmaceutical formulation for use in the disclosed methods includes bupivacaine linolenate, at least one thermosensitive polymer, and at least one mucoadhesive or dermoadhesive agent. In some embodiments of the disclosed methods, the disease or condition is oral mucositis. In some embodiments, the composition may be administered to the mucosa or skin. In certain embodiments, the composition may be administered by transmucosal delivery, sublingual delivery, via the buccal cavity, via mucosal membranes, or via the gastrointestinal tract. In some embodiments, the composition is administered as a spray formulation. In certain embodiments, the composition may be administered as four to seven sprays of the spray formulation. In other embodiments, more or less sprays of the spray formulation are administered, depending on the desired dose and the concentration of the bupivacaine linoleate in the formulation. In some embodiments, the composition releases bupivacaine linoleate, bupivacaine linolenate or bupivacaine laurate for up to about 2 hours to about 6 hours.

In some embodiments of the disclosed methods, the pharmaceutical formulation used in the methods includes bupivacaine linoleate at a concentration of about 0.5 mg/mL to about 10 mg/mL or about 0.1% weight/volume (w/v) to about 2% w/v of the formulation. In some embodiments of the disclosed methods, the pharmaceutical formulation used in the methods includes bupivacaine linolenate at a concentration of about 0.5 mg/mL to about 13 mg/mL or about 0.1% weight/volume (w/v) to about 2% of the formulation. In one aspect, the bupivacaine linoleate is present at a concentration of about 2 mg/mL or 0.4% w/v of the formulation. In another aspect, the bupivacaine linolenate is present at a concentration of about 12 mg/mL or 1.2% w/v of the formulation. In certain embodiments, at least one thermosensitive polymer is poloxamer or poloxamine. In some embodiments, the thermosensitive polymer is present at a concentration of about 10% w/v to about 22% w/v of the formulation. In some embodiments, the pharmaceutical formulation used in the methods includes two or more thermosensitive polymers. In certain embodiments, the pharmaceutical formulation used in the methods includes poloxamer 407 and poloxamer 188. In some embodiments, the pharmaceutical formulation used in the methods may be a liquid at about 25° C. and forms a semi-solid gel at about 37° C. In certain embodiments, the pharmaceutical formulation used in the methods has a gelation temperature of about 30° C. to about 37° C. In some embodiments of the methods, the mucoadhesive or dermoadhesive agent used in the pharmaceutical formulation is selected from the group consisting of polyethylene glycol, caprylic glyceride, capric glyceride, vinyl polymer, methyl cellulose, ethyl cellulose, hydroxyethyl cellulose, hydroxypropyl cellulose, hydroxypropylmethyl cellulose, carboxymethyl cellulose, alginic acid, sodium alginate, acrylic acid polymer, and carbopol polymer. In some embodiments, the mucoadhesive or dermoadhesive agent comprises carboxymethylcellulose. In a particular embodiment, the mucoadhesive or dermoadhesive agent is present in pharmaceutical formulation at a concentration of about 0.05% w/v to about 5% w/v of the formulation. In some embodiments, the mucoadhesive or dermoadhesive agent includes at least one acrylic acid polymer or carbopol polymer. In certain embodiments, the acrylic acid polymer or carbopol polymer may be present at a concentration of about 0.04% w/v to about 1% w/v of the formulation. In some embodiments, the pharmaceutical formulation used in the methods includes bupivacaine linoleate, poloxamer 407, poloxamer 118, and Carbopol® 971P (an acrylic acid polymer). In some embodiments, the composition includes bupivacaine linoleate, poloxamer 407, poloxamer 118, and Carbopol® 974P (an acrylic acid polymer). In some embodiments, the composition includes bupivacaine linoleate, poloxamer 407, poloxamer 118, and Noveon® AA-I polycarbophil (an acrylic acid polymer). In some embodiments, the composition includes bupivacaine linolenate, poloxamer 407, poloxamer 118, and Carbopol® 974P (an acrylic acid polymer). In some embodiments, the compositions include at least one pharmaceutically acceptable excipient, such as a flavoring agent, sweetener, sweet cohancer, preservative, stabilizer, or solubilizer.

Disclosed are materials, compositions, and ingredients that can be used for, can be used in conjunction with, can be used in preparation for, or are products of the disclosed embodiments. These and other materials are disclosed herein, and it is understood that when combinations, subsets, interactions, groups, etc. of these materials are disclosed that while specific reference of each various individual and collective combinations and permutations of these compositions may not be explicitly disclosed, each is specifically contemplated and described herein. For example, if a method is disclosed and discussed, and a number of modifications that can be made to a number of molecules included in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties. The following description provides further non-limiting examples of the disclosed compositions and methods.

EXAMPLES

Example 1

Preparation of Formulations

In order to obtain a formulation suitable for the long-acting release of the anesthetic, a number of different formulations were prepared as shown in Table 1. Poloxamer 407 (NF) and poloxamer 118 (NF) were purchased from Spectrum Chemical Manufacturing Corp. Carbopols® (971P NF and 974P NF) and Noveon® AA-1 polycarbophil (USP grade) were gifted by Lubrizol Corp. Bupivacaine linoleate and bupivacaine linolenate were gifted by Cellix Bio.

The blank formulations (i.e., formulations without the bupivacaine linoleate) were prepared by homogeneous mixing different amounts of poloxamer 407, poloxamer 118, and Carbopols® or Noveon® AA-1 polycarbophil in water at 4° C. The solution was adjusted to a final pH of 6.5±0.3 by NaOH solution (1 M). Bupivacaine linoleate, bupivacaine linolenate or bupivacaine laurate was dissolved in dimethyl sulfoxide (DMSO) at 37±1° C. Bupivacaine linoleate loaded formulations were prepared by adding the bupivacaine linoleate DMSO solution dropwise into the vigorously stirred blank formulations at different temperatures. Likewise, the bupivacaine linolenate loaded formulations were prepared by adding the bupivacaine linolenate DMSO solution dropwise into the vigorously stirred blank formulations at different temperatures. The stirring speed was set at 850 rpm, and the stirring time was 2 hours. As shown in FIG. 1, a low temperature of 4±1° C. led to drug precipitation in some formulations; therefore, a temperature of 22±1° C. was preferred for the drug loading procedure.

Gelation temperatures of the formulations were measured by a tube inversion method. The test-tubes containing the formulations were inverted at different temperatures, and the time until no fluidity was observed. As shown in Table 1, the poloxamer solutions exhibited substantially different gelation temperatures at different combinations of ingredient concentrations (Formulations 1-3). Carbopols® and Noveon® AA-1 polycarbophil are universal mucoadhesive polymers that can be used for many dosage forms, such as tablets, solutions, gels, and pastes. The addition of a mucoadhesive polymer slightly altered the gelation temperature (Formulations 4-6). It was shown that a high concentration (5 mg/mL to 8 mg/mL) of bupivacaine linoleate reduced the gelation temperature (Formulations 7-10). Therefore, the concentration of the poloxamers must be adjusted accordingly with higher drug loading.

TABLE 1

Gelation temperature of formulations.

| | Formulation | | | | | | | | | |
|---|---|---|---|---|---|---|---|---|---|---|
| | 1 | 2 | 3 | 4 | 5 | 6 | 7 | 8 | 9 | 10 |
| Poloxamer 407 wt. % | 18 | 17.7 | 17.6 | 16.5 | 16.5 | 16.5 | 16.5 | 16.5 | 16.5 | 16.5 |
| Poloxamer 118 wt. % | 0 | 1.6 | 2.4 | 4.7 | 4.7 | 4.7 | 4.7 | 4.7 | 4.7 | 4.7 |
| Carbopol ® 971P wt .% | — | — | — | 0.04 | — | — | — | 0.04 | — | — |
| Carbopol ® 974P wt. % | — | — | — | — | 0.08 | — | — | — | 0.08 | — |
| Noveon ® AA-1 wt. % | — | — | — | — | — | 0.08 | — | — | — | 0.08 |
| Bupivacaine Linoleate mg/mL | — | — | — | — | — | — | 6.7 | 6.8 | 7.3 | 6.1 |
| DMSO v/v % | — | — | — | — | — | — | 0.1 | 0.1 | 0.1 | 0.1 |
| Gelation temperature ° C. | 25 | 30 | 33 | 42 | 40 | 40 | 36 | 34 | 33 | 33 |

Example 2

Adhesion Properties of the Bupivacaine Linoleate Formulations

Oral mucosa adhesion properties were tested using TA.XT plus Texture Analyzer. Fresh porcine buccal mucosa was attached to a probe using tissue adhesive glue. About 1 mL of each formulation was placed on the hot plate at temperature of 37±1° C. The probe with porcine buccal mucosa attached was moved downward to allow full contact with the formulation on the hot plate at specific force and maintained for a specific time. The probe was subsequently withdrawn at a specific test speed. The maximum force required to separate the probe from the formulation was detected by the instrument, and the work of adhesion was calculated from the area under the curve of force versus distance.

Figure 2:
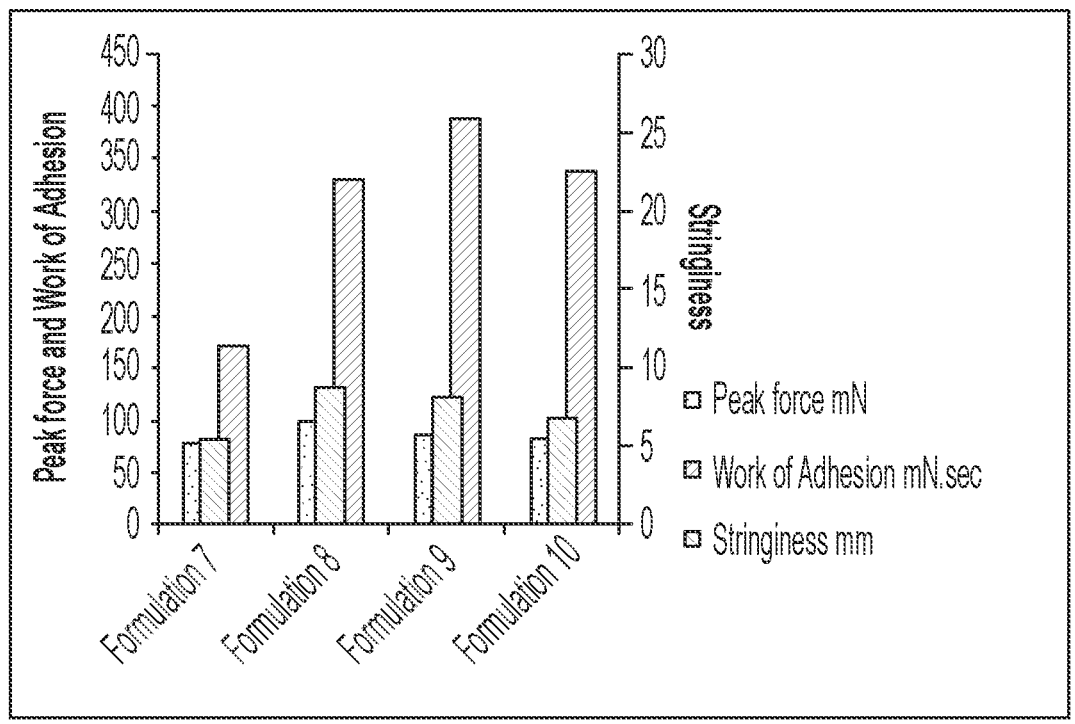
FIG. 2 is a graph showing the oral mucosa adhesion properties of four formulations containing bupivacaine linoleate. For each of the four formulations listed on the x axis, the peak force (mN), work of adhesion (mN/sec), and stringiness (mm) were measured, and the measurements are shown by the left, middle, and right bars, respectively.

The results of these experiments are shown in FIG. 2. The bar graph shows the oral mucosa adhesion properties of four formulations containing bupivacaine linoleate. For each of the four formulations listed on the x axis, the peak force (mN), work of adhesion (mN/sec), and stringiness (mm) were measured, and the measurements are shown by the left, middle, and right bars, respectively. Formulation 7 was a control formulation that did not include a mucoadhesive agent, and Formulations 8-10 included different mucoadhesive agents.

Example 3

Sustained Release of Bupivacaine Linoleate

An in vitro release study for the formulations was performed using an USP apparatus 2 (Sotax AT7 smart Dissolution Apparatus, USA) with enhancer cells (exposure area of 4 cm², Agilent Technologies, USA). The reservoir of the enhancer cells (approximately 1.5 mm depth) was filled by the formulations (0.5 mL). 50 mL dissolution medium was added to the dissolution vessels. The rotating speed of the mini-paddles was set at 100 rpm. At predetermined time intervals, 1 mL of the release medium was withdrawn and replenished with fresh media. All of the dissolution tests were conducted in pH 5.7±0.1 PBS (50 mM).

Figure 3:
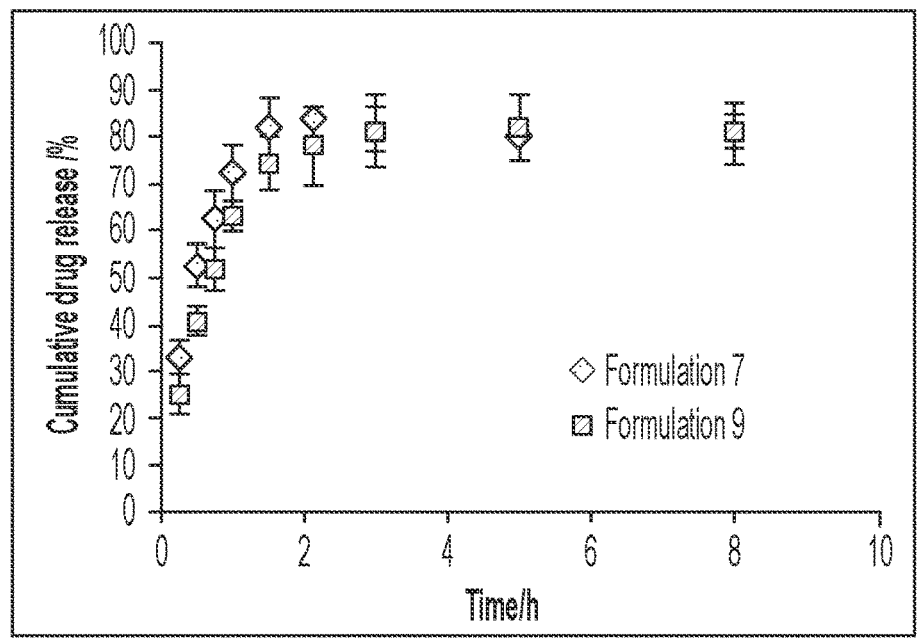
FIG. 3 is a graph showing the release of bupivacaine linoleate from two formulations over time. The time in hours is measured on the x axis, and the drug release in % is measured on the y axis. Results for the first formulation (Formulation 7) are shown with the diamonds, and the results for the second formulation (Formulation 9) are shown with the squares.

The results of an in vitro release study with two of the formulations containing bupivacaine linoleate are shown in FIG. 3. The time in hours is measured on the x axis, and the drug release in % is measured on the y axis. Results for the first formulation (Formulation 7, which contains bupivacaine linoleate and a thermosensitive polymer, but not a mucoadhesive polymer) are shown with the diamonds, and the results for the second formulation (Formulation 9, which contains bupivacaine linoleate, a thermosensitive polymer, and a mucoadhesive polymer) are shown with the squares. As shown in FIG. 3, the release of bupivacaine linoleate from the formulations with or without mucoadhesive polymers was nearly linear in the first 1.5 hours and reached a plateau at about 2 hours. At 1.5 hours, approximately 82% of bupivacaine linoleate was released from the formulation without Carbopol® 974P, and approximately 74% was released from the formulation with Carbopol® 974P. These data show that the addition of mucoadhesive polymers to the bupivacaine linoleate formulation slightly extended the duration of the drug release from the formulation.

Example 4

Treatment of Oral Mucositis with Bupivacaine Linoleate Composition

A 55 year old male patient with head and neck cancer is undergoing radiation therapy with concurrent weekly chemotherapy. The patient develops ulcerative oral mucositis, which is very painful. The patient uses a handheld sprayer to administer the spray directly to the region of ulceration in the oral mucosa. The composition is a liquid spray formulation that includes bupivacaine linoleate, a thermosensitive polymer agent, and a mucoadhesive polymer agent. Upon administration, the composition forms a semi-solid gel that adheres to the oral mucosa, providing a protective barrier and releasing bupivacaine over time. The composition provides local anesthetic relief from the pain associated with oral mucositis for about two to four hours.

Example 5

Preparation Method Achieving High Drug Loading and Stability

1. Improved Preparation Method Achieving High Drug Loading of 10-13 mg/mL

Materials: Poloxamer 407 (NF) and poloxamer 118 (NF) were purchased from three sources: Spectrum Chemical Manufacturing Corp., BASF Pharma Ingredients and Sigma-Aldrich. Sodium dodecyl sulfate was purchased from Sigma-Aldrich. Bupivacaine linolenate was gifted by Cellix Bio. All other materials were from the same sources as stated in the original application.

Method: Blank formulation preparation: Carbopols or polycarbophil was dissolved to form a homogeneous solution at 20-25° C. Poloxamers were added to the solution at 2-8° C. The solution was adjusted to a final pH of 5.0-6.5 using NaOH solution (10 M).

Method: Drug loading: Bupivacaine linoleate, bupivacaine linolenate or bupivacaine laurate was dissolved in dimethyl sulfoxide (DMSO) at 40±1° C. Bupivacaine linoleate, bupivacaine linolenate or bupivacaine laurate in DMSO solution was then added dropwise into the vigorous stirred blank formulations, followed by the addition of sodium dodecyl sulfate (SDS) powder at a final concentration of 0.8-1.2% w/v. The stirring speed was set at 850 rpm and the stirring time was 2 hours. Flavoring agent was added at the end and a homogeneous opaque solution was obtained.

Figure 4:
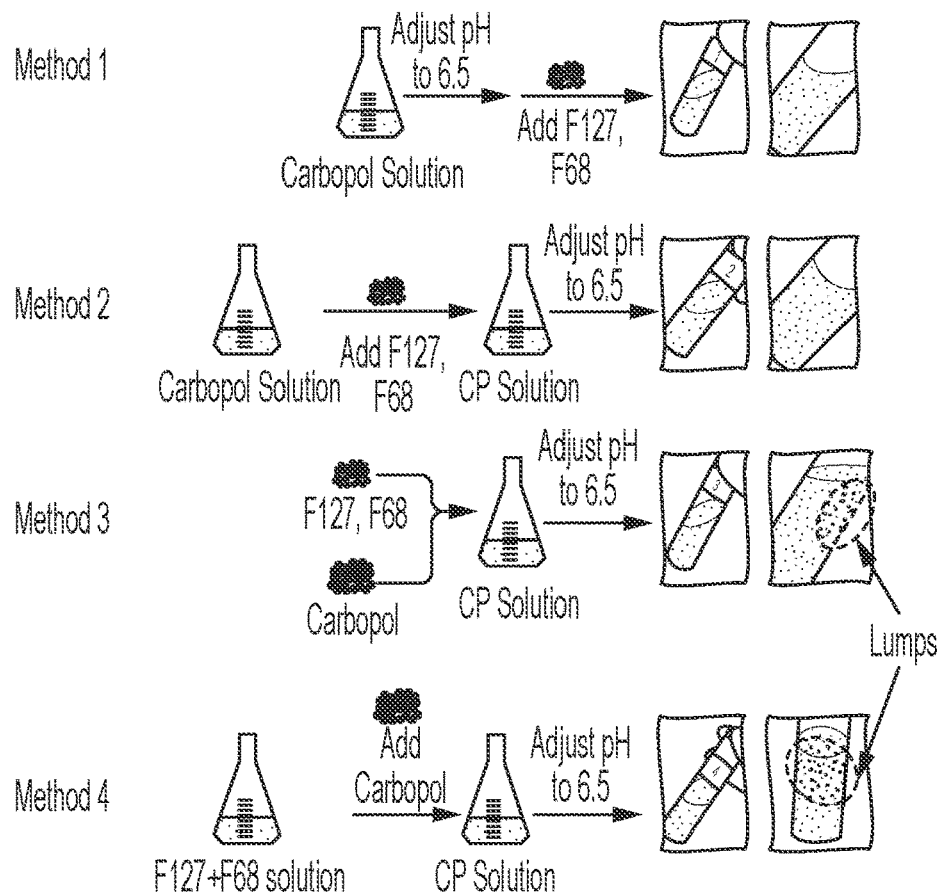
FIG. 4 is a flow chart with photographs showing blank formulations prepared by four different methods.

Result: As shown in FIG. 4, blank formulations were prepared using four different preparation methods. The total time required to obtain a homogeneous solution was 24 hours, 6 hours, 1 week, and 1 week for Method 1, Method 2, Method 3 and Method 4, respectively. Therefore, the most time-saving method to prepare a blank formulation was Method 2.

Two different methods were attempted to incorporate SDS into the formulation, shown in FIG. 5A. In method 1, bupivacaine salt in DMSO was added dropwise into the formulation after SDS powder was completely dissolved in the blank formulation. In method 2, bupivacaine salt in DMSO was first added to the blank formulation to form a homogeneous suspension under vigorous stirring. SDS powder was added quickly after a homogeneous suspension was observed. Separated droplets floating on top of the formulation were observed in method 1. An opaque solution was obtained using method 2. Pure bupivacaine linolenate and formulation prepared via method 2 with bupivacaine linolenate were observed using polarized light microscopy, shown in FIG. 5B. The crystalline form of pure bupivacaine linolenate was confirmed. However, no crystals were observed outside the formulation, indicating successful drug loading within the formulation using method 2. Consequently, method 2 was selected to prepare high drug loading formulations (10-13 mg/mL).

SDS was dissolved in the formulation as a solubilizing agent. Five formulations with or without SDS are shown in Table 2. The addition of 0.5% w/v SDS increased the drug loading from 7.39 mg/mL to 9.82 mg/mL. Increasing the amount of sodium dodecyl sulfate from 0.5% w/v to 0.8% w/v increased the drug loading from 9.82 mg/mL to 12.30 mg/mL. The addition of 0.5% w/v mint flavor or raspberry flavor did not affect the drug loading or gelation temperature of the formulation.

TABLE 2

Drug loading and gelation temperature of example formulations

| | Formulation | | | | |
|---|---|---|---|---|---|
| | CP | SCP-1 | SCP-2 | SCP-2 mint flavored | SCP-2 raspberry flavored |
| Poloxamer 407 wt. % | 16.5 | 16.5 | 12.9 | 12.9 | 12.9 |
| Poloxamer 118 wt. % | 4.7 | 4.7 | 5.6 | 5.6 | 5.6 |
| Carbopol ® 974P wt. % | 0.1 | 0.1 | 0.1 | 0.1 | 0.1 |
| Sodium dodecyl sulfate wt. % | — | 0.5 | 0.8 | 0.8 | 0.8 |
| Flavoring powder wt. % | — | — | — | 0.5 | 0.5 |
| Bupivacaine Linolenate mg/ml | 7.39 | 9.82 | 12.30 | 12.48 | 12.60 |
| Gelation temperature ° C. | 32.2 | 27.3 | 32.2 | 33.0 | 32.6 |

2. Stability of the Formulation

Method: The stability of the formulations was investigated at different storage conditions with temperature ranging from 25-40° C. Critical attributes were studied at storage times up to 3 months. Formulations were sealed in 10 mL impermeable glass vials under ambient humidity conditions. At predetermined storage time, formulations were allowed to relax at room temperature for 1 hour before testing for critical attributes. Drug loading was tested by high performance liquid chromatography (HPLC). Polarized light microscopy was used to detect drug precipitation. Rheological properties of the formulations were tested using a Rheometer. Drug release testing was performed using USP apparatus 2 with enhancer cells at 100 rpm, 37° C.

Results: Formulation SCP-2 was tested for stability at different storage conditions. The appearance of the formulation did not change at these storage conditions (FIG. 6). There was no birefringence detected under polarized light microscopy, indicating no crystalline drug present. Air bubbles (bright circles) gradually reduced during storage.

Figure 7:
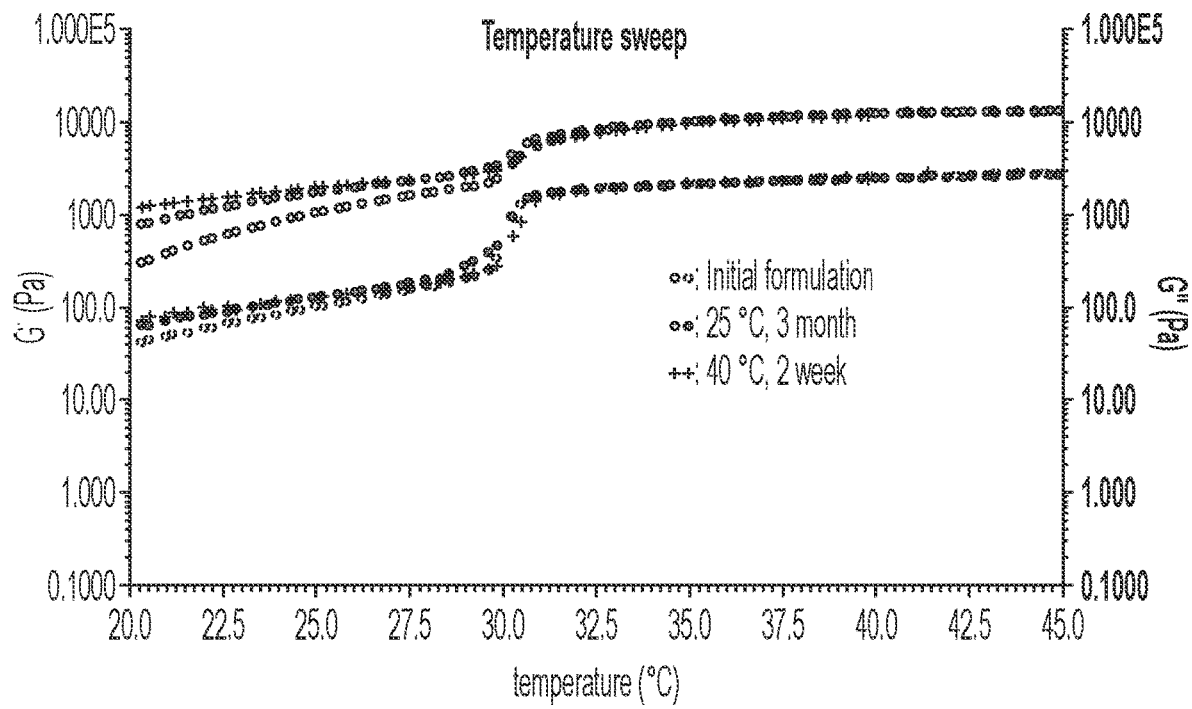
FIG. 7 is a graph showing the rheological properties (G' and G") of formulation SCP-2 at different storage conditions.

Drug loading, pH as well as specific gravity did not show major changes under the storage conditions investigated (Table 3). The gelation temperature increased slightly from 32.2° C. to 34.1° C. after 3 months storage at 25° C. and to 33.7° C. after 2 weeks storage at 40° C. Nevertheless, the gelation temperature was still 2.9-3.3° C. lower than the oral temperature 37° C., indicating a gelation would take place on contact with the oral mucosa. Temperature sweep at 20-45° C. was performed to investigate the impact of gelation temperature on the rheological properties of formulations (FIG. 7). Neither storage modulus G' nor loss modulus G" were altered at 37° C. This revealed that the gel strength at the oral temperature would not be altered although the gelation temperature was slightly increased. The storage modulus of formulations at room temperature (liquid form) increased during storage. An increase of both G' and G" was observed at a temperature of 30-31° C., which agreed with the gelation temperature tested by the tube inversion method, as shown in Table 3. The differences were due to the intrinsic errors between the techniques or methods.

TABLE 3

Some critical attributes of formulation SCP-2 at different storage conditions

| | Storage Condition | | |
|---|---|---|---|
| | Initial formulation | 25° C. 3 months | 40° C. 2 weeks |
| Bupivacaine Linolenate mg/mL | 12.30 | 11.56 | 12.33 |
| PH | 7.25 | 7.22 | 7.24 |
| Specific gravity | 1.014 | 1.014 | 1.014 |
| Gelation temperature ° C. | 32.2 | 34.1 | 33.7 |

Figure 8:
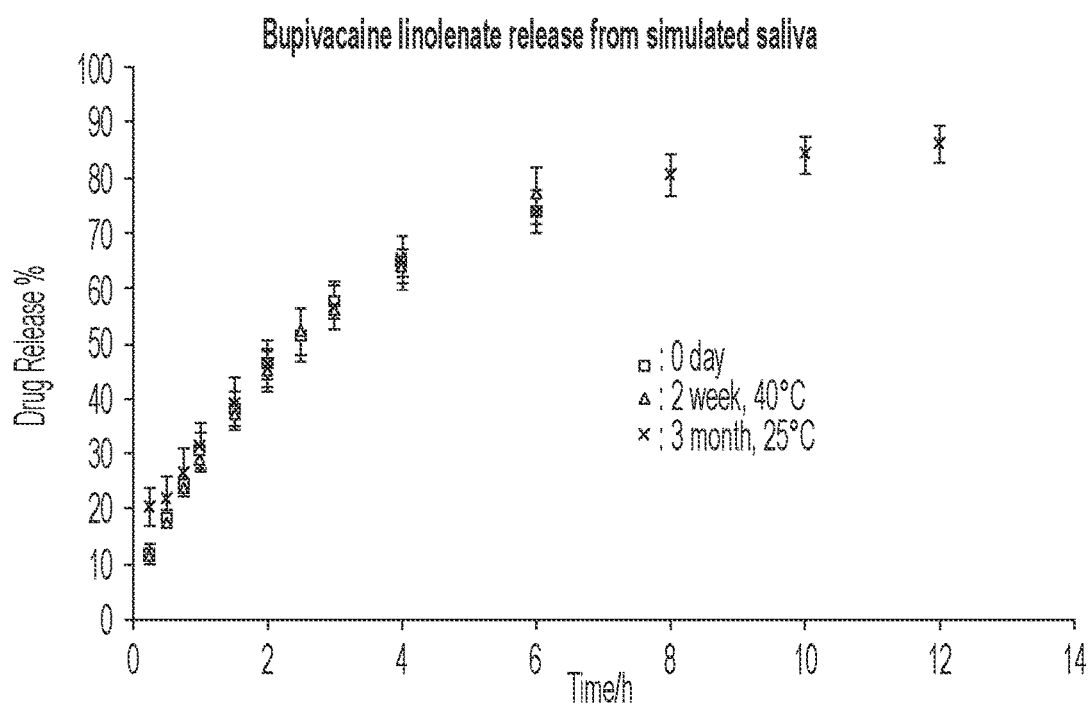
FIG. 8 is a graph showing the results of drug release testing of formulation SCP-2 at different storage conditions. Bupivacaine linolenate was released from the formulations into simulated saliva (pH 6.8±0.1).

The release of bupivacaine linolenate from formulation SCP-2 in simulated saliva was shown in FIG. 8. Formulations at the listed storage conditions showed the same release profiles except that the formulation stored at 25° C. for 3 months showed a slightly higher initial release at 15-30 min. This was due to the small increase in the gelation temperature as shown in Table 3. Formulations with high drug loading (10-13 mg/mL) showed slower release compared to those with low drug loading (6.7-7.3 mg/mL in FIG. 3). At 1.5 hours, drug release was 74-82% from low drug loading formulations (6.7-7.3 mg/ml, formulation 7 and formulation 9, FIG. 3) whereas drug release was 31-39% from the high drug loading formulations (11.56-12.33 mg/ml). The decrease in the release rate was a result of complicated formulation changes including the concentration of F127 and F68, the addition of SDS surfactant as well as the drug loading of bupivacaine linolenate.

What is claimed is:

1. A method for treating a subject suffering from oral mucositis, aphthous stomatitis, pemphious vulgaris, or mucous membrane pemphigoid, the method comprising the step of administering to a subject suffering from oral mucositis, aphthous stomatitis, pemphigus vulgaris, or mucous membrane pemphigoid, a therapeutically effective amount of an oral spray formulation comprising an anesthetic, at least one thermosensitive polymer, and a mucoadhesive or dermoadhesive agent, wherein the anesthetic comprises bupivacaine hydrochloride and the mucoadhesive or dermoadhesive agent comprises carboxymethylcellulose and further wherein: (a) the concentration of bupivacaine hydrochloride in the formulation is about 0.05% weight/volume (w/v) to about 5% w/v of the formulation; (b) the concentration of at least one thermosensitive polymer is about 10% w/v to about 22% w/y of the formulation; (c) the concentration of the mucoadhesive or dermoadhesive agent is about 0.05% w/y to about 5% w/y of the formulation; and (d) the thermosensitive polymer comprises poloxamer 407, poloxamer 188, or a combination thereof.

2. The method of claim 1, wherein the subject is suffering from oral mucositis.

3. The method of claim 1, wherein the subject is suffering from aphthous stomatitis.

4. The method of claim 1, wherein the subject is suffering from pemphigus vulgaris.

5. The method of claim 1, wherein the subject is suffering from mucous membrane pemphigoid.

6. The method of claim 1, wherein the thermosensitive polymer comprises poloxamer 407.

7. The method of claim 1, wherein the thermosensitive polymer comprises poloxamer 188.

8. The method of claim 1, wherein the thermosensitive polymer comprises poloxamer 407 and poloxamer 188.

9. The method of claim 1, wherein about 80% of the anesthetic is released from the oral spray formulation within 2 hours after administration to the subject.

10. The method of claim 1, wherein the oral spray formulation is a liquid at about 25° C. and forms a semi-solid gel at about 37° C.

11. The method of claim 1, wherein the oral spray formulation comprises a gelation temperature of about 30° C. to about 37° C.

12. The method of claim 1, wherein the oral spray formulation releases the anesthetic for up to about 2 hours to about 6 hours.

* * * * *